US008907665B2

(12) United States Patent
Rose et al.

(10) Patent No.: US 8,907,665 B2
(45) Date of Patent: Dec. 9, 2014

(54) MAGNETOSTRICTIVE SENSOR ARRAY FOR ACTIVE OR SYNTHETIC PHASED-ARRAY FOCUSING OF GUIDED WAVES

(75) Inventors: Joseph L. Rose, State College, PA (US); Jason K. Van Velsor, Boalsburg, PA (US); Steven E. Owens, Bellefonte, PA (US); Roger L. Royer, Jr., Williamsburg, PA (US)

(73) Assignee: FBS, Inc., State College, PA (US)

( * ) Notice: Subject to any disclaimer, the term of this patent is extended or adjusted under 35 U.S.C. 154(b) by 527 days.

(21) Appl. No.: 13/298,758

(22) Filed: Nov. 17, 2011

(65) Prior Publication Data

US 2012/0119732 A1    May 17, 2012

Related U.S. Application Data

(60) Provisional application No. 61/414,553, filed on Nov. 17, 2010.

(51) Int. Cl.
*G01N 27/82* (2006.01)
*G01N 29/26* (2006.01)
*G01N 29/24* (2006.01)

(52) U.S. Cl.
CPC .......... *G01N 29/262* (2013.01); *G01N 29/2412* (2013.01); *G01N 2291/0425* (2013.01)
USPC ......................................... 324/240; 324/228

(58) Field of Classification Search
USPC ................................................ 324/228, 240
See application file for complete search history.

(56) References Cited

U.S. PATENT DOCUMENTS

| 2,063,948 | A | 12/1936 | Pierce et al. |
| 5,581,037 | A | 12/1996 | Kwun et al. |
| 6,396,262 | B2 | 5/2002 | Light et al. |
| 6,429,650 | B1 | 8/2002 | Kwun et al. |
| 7,573,261 | B1 | 8/2009 | Vinogradov |
| 7,614,313 | B2 | 11/2009 | Kim et al. |
| 7,997,139 | B2 * | 8/2011 | Owens et al. ............ 73/622 |

OTHER PUBLICATIONS

Z. Sun, L. Zhang, and J.L. Rose, Flexural Torsional Guided Wave Pipe Inspection, Review of Quantitative Nondestructive Evaluation, 2006, pp. 181-186, vol. 25, American Institute of Physics, U.S.
Takahiro Hayashi and Morimasa Murase, Defect Imaging With Guided Waves in a Pipe, J. Acoust. Soc. Am., Apr. 2005, pp. 2134-2140, vol. 117, Acoustical Society of America, U.S.
Jian Li and Joseph L. Rose, Angular-Profile Tuning of Guided Waves in Hollow Cylinders Using a Circumferential Phased Array, IEEE Transactions on Ultrasonics, Ferroelectrics, and Frequency Control, Dec. 2002, pp. 1720-1729, vol. 49, No. 12, IEEE, U.S.

(Continued)

Primary Examiner — Reena Aurora
(74) Attorney, Agent, or Firm — Duane Morris LLP

(57) ABSTRACT

A system includes at least one strip of ferromagnetic material and a plurality of pulsing/receiving coil circuits. The at least one strip of ferromagnetic material is induced with a bias magnetic field and is coupled to a surface of a structure under test. The plurality of pulsing/receiving coil circuits are aligned with a surface of the at least one strip of the ferromagnetic material. The plurality of pulsing/receiving coil circuits are individually controllable by a number of channels to excite guided waves in the structure under test using at least one of active phased-array focusing or synthetic phased-array focusing of the guided waves.

20 Claims, 8 Drawing Sheets

(56) References Cited

OTHER PUBLICATIONS

Jing Mu, Li Zhang, Jia Hua, and Joseph L. Rose, Pipe Testing With Ultrasonic Guided Wave Synthetic Focusing Techniques, Materials Evaluation, Oct. 2010, pp. 1171-1176.

Fey Yan, Roger L. Royer, Jr. and Joseph L. Rose, Ultrasonic Guided Wave Imaging Techniques in Structural Health Monitoring, Journal of Intelligent Material Systems and Structures, vol. 0, 2009.

* cited by examiner

MAGNETOSTRICTIVE SENSOR ARRAY FOR ACTIVE OR SYNTHETIC PHASED-ARRAY FOCUSING OF GUIDED WAVES

CROSS-REFERENCE TO RELATED APPLICATIONS

This application claims priority to U.S. Provisional Application No. 61/414,553, which was filed on Nov. 17, 2010 and is herein incorporated by reference in its entirety.

FIELD OF DISCLOSURE

The disclosed system and method relate to detecting and locating defects in a material. More specifically, the disclosed system and method relate to detecting and locating defects in a material through the use of guided waves.

BACKGROUND

Non-destructive testing (NDT) and structural health monitoring (SHM) techniques are frequently used to test or inspect a material without causing damage. For example, such NDT/SHM techniques may be used to inspect welds or identify defects in pipes, airplane components, and other devices or materials in which maintaining the integrity of (i.e., not damaging) the device or material is desirable. For the purposes of the present technology, NDT refers to the non-invasive inspection of a structure or component, usually in spaced time intervals, and SHM refers to the permanent installation of a sensor for long-term monitoring of the structure or component.

Guided waves are a specific method for the NDT/SHM of structures or components in which low-frequency (generally <1 MHz) ultrasonic waves are introduced into the structure that subsequently interact with the local boundaries of the structure and form a coherent propagating wave packet that then follows the structure. Such boundaries may be the external surfaces of a particular material or the boundary may be an interface between two materials. The propagation characteristics of the wave packet are dictated by the dimensions and material properties of the structure. Unlike traditional ultrasonic waves that may be used to performed localized testing or inspection, guided waves may be used to perform remote testing or inspection of a material through various NDT/SHM techniques. In the pulse-echo guided wave technique, appurtenances such as welds, structural attachments, cracks, or metal loss reflect portions of the wave packet back toward the generating sensor where it is received by the generating sensor or by a separate receiving sensor and then amplified, digitized, processed, and displayed. These reflections may be analyzed to determine the extent of the abnormality or defect as well as the location of such abnormality or defect.

Magnetostrictive guided wave methods refer to the utilization of the magnetostrictive effect to generate or the inverse magnetostrictive effect to receive guided waves directly in the structure being inspected or in a piece of magnetostrictive material temporarily or permanently attached to the structure being inspected. The magnetostrictive effect refers to the tendency of a ferromagnetic material to change shape when subjected to a magnetic field. By controlling the time-varying properties of the magnetic field, the magnetostrictive material can be made to oscillate in such a fashion as to generate a propagating guided wave.

Current magnetostrictive methods used for pipe inspection generally consist of a non-segmented dual-element sensor that is capable of directional control only. Conventional magnetostrictive pipe inspection methods suffer from several significant disadvantages. For example, conventional magnetostrictive methods do not allow for the ability to separate wave modes that are distributed evenly around the pipe circumference (axisymmetric modes) from those that are unequally distributed around the pipe circumference (flexural modes). Many structural features, such as welds and clamps, produce axisymmetric wave reflections while metal-loss defects generally produce flexural wave reflections. Consequently, the inability to distinguish between axisymmetric modes and flexural modes render these structural features indistinguishable from corrosion and other metal-loss defects.

Another significant drawback of conventional methods is that they do not enable information regarding the circumferential extent or location of a metal-loss defect to be determined. For example, it is therefore not possible to determine if a 15% loss in the cross-sectional area (CSA) of a pipe at a specific axial location occurs over 25% of the pipe circumference or over 80% of the pipe circumference; two different conditions that would lead to two entirely different integrity states.

SUMMARY

In some embodiments, a system includes at least one strip of ferromagnetic material and a plurality of pulsing/receiving coil circuits. The at least one strip of ferromagnetic material is induced with a bias magnetic field and is coupled to a surface of a structure under test. The plurality of pulsing/receiving coil circuits are aligned with a surface of the at least one strip of the ferromagnetic material. The plurality of pulsing/receiving coil circuits are individually controllable by a number of channels to excite guided waves in the structure under test using at least one of active phased-array focusing or synthetic phased-array focusing of the guided waves.

In some embodiments, a non-destructive inspection method includes inducing a bias magnetic field in a ferromagnetic material that is coupled to a surface of a test structure. A plurality of channels are individually address to actuate a plurality of pulser/receiver coils disposed on the ferromagnetic material to generate guided waves in the test structure using at least one of active phased-array focusing or synthetic phased-array focusing of the guided waves. A reflected signal is received at one of the plurality of pulser/receiver coils, and the reflected signal is processed to identify if the test structure includes an irregularity along its longitudinal length.

In some embodiments, a system includes a ferromagnetic material coupled to a surface of a test piece. The ferromagnetic material has an induced bias magnetic field. A plurality of pulsing/receiving coil circuits are distributed on the surface of the test piece and are aligned to a surface of the ferromagnetic material. A controller is configured to individually control each of a plurality of channels each corresponding to at least one of the plurality of pulsing receiving coil circuits to excite guided waves in the test piece using at least one of active phased-array focusing or synthetic phased-array focusing of the guided waves.

DETAILED DESCRIPTION

This description of the exemplary embodiments is intended to be read in connection with the accompanying drawings, which are to be considered part of the entire written description.

The improved non-destruction inspection systems and methods described herein advantageously enable the generation and reception of flexural guided wave modes using segmented magnetostrictive sensors for the inspection of hollow cylindrical structures as well as plate and plate-like structures. As used herein, "plate-like structures" may include, but are not limited to, structures with some curvature but not so much such that the ratio of the inner curvature to that of the outer curvature is less than 0.8. The segmentation of the magnetostrictive sensors make it possible to distinguish reflections generated by structural features, such as welds, from reflections generated by material defects, such as metal loss. Phased-array and synthetic guided wave focusing concepts can be employed using the segmented magnetostrictive sensor to determine the approximate circumferential location and extent of a reflection source thereby providing significantly improved sizing capabilities compared to conventional magnetostrictive sensors. By employing the focusing concepts with the segmented magnetostrictive sensor, improved signal-to-noise ratios (SNR) can be achieved through constructive interference of the wave energy generated and/or received by the individual segments of the sensor. This improvement in SNR can lead to improved sensitivity and penetration power.

Figure 1A:
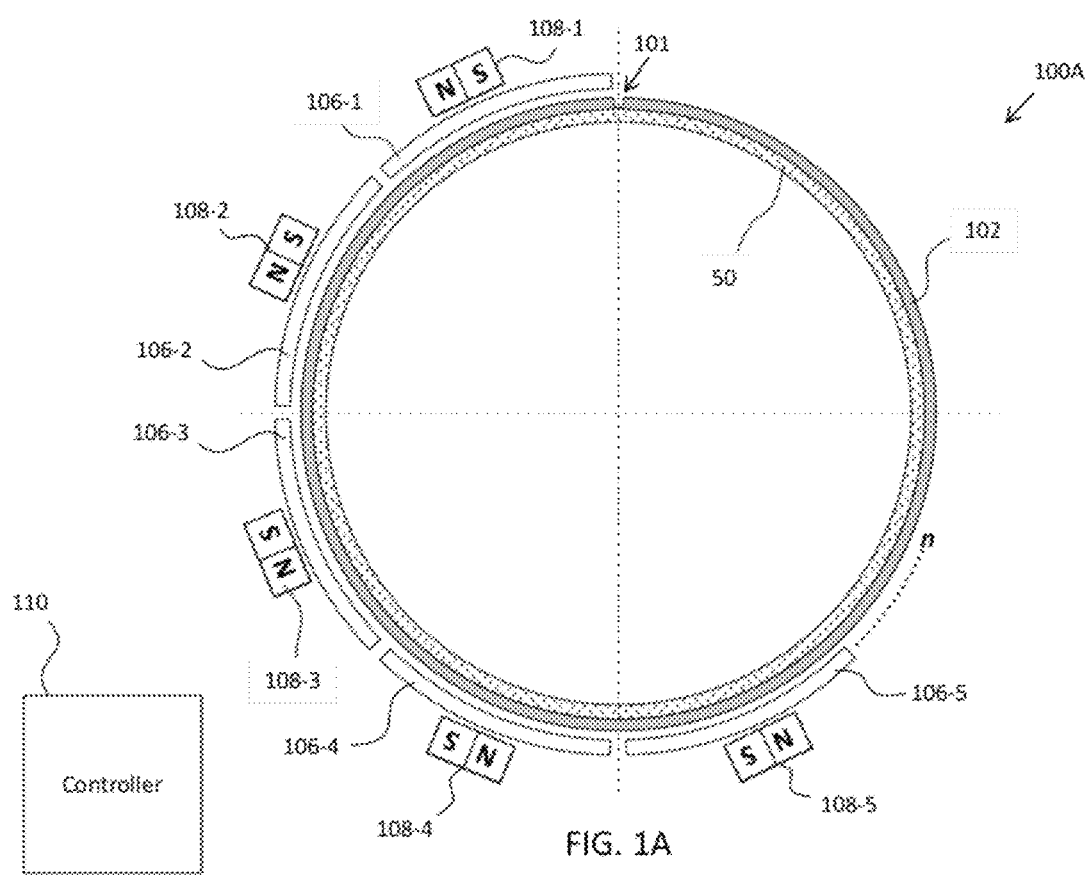
FIG. 1A illustrates one example of an improved magnetostriction inspection/testing system.
Figure 1B:
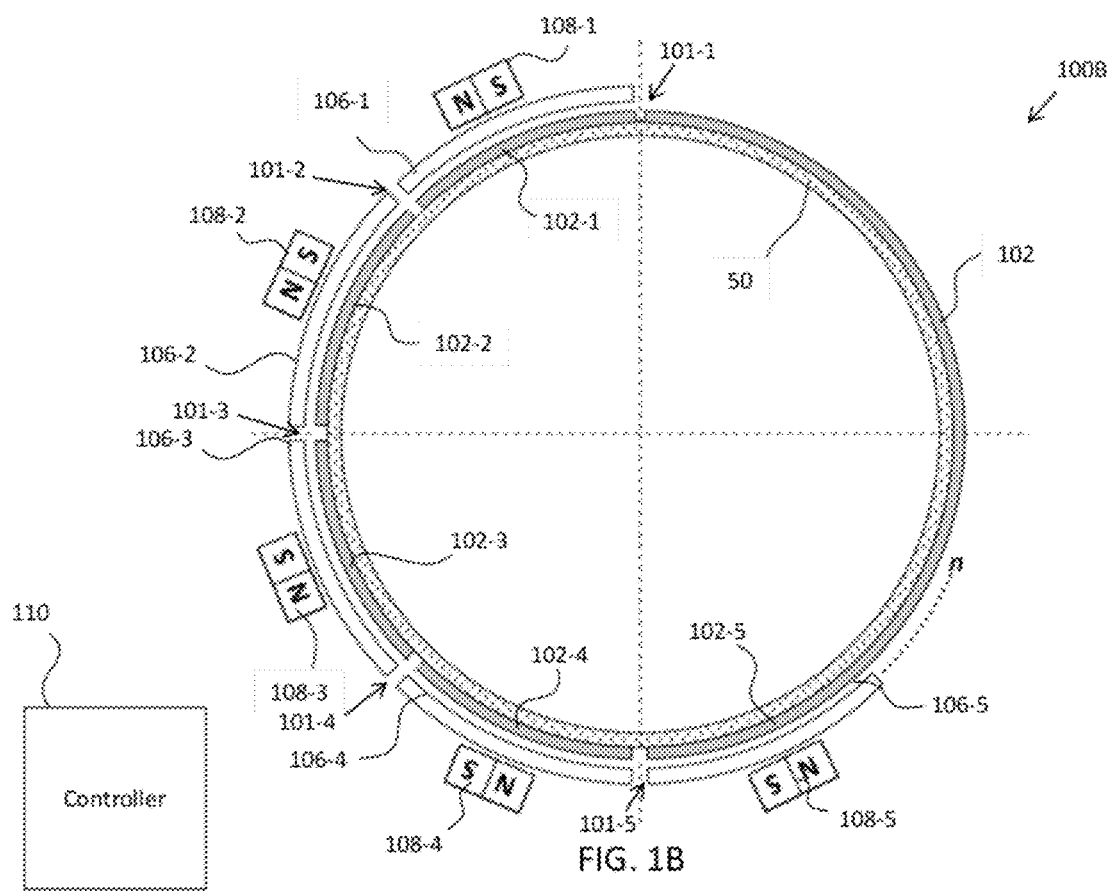
FIG. 1B illustrates another example of an improved magnetostriction inspection/testing system.
Figure 1C:
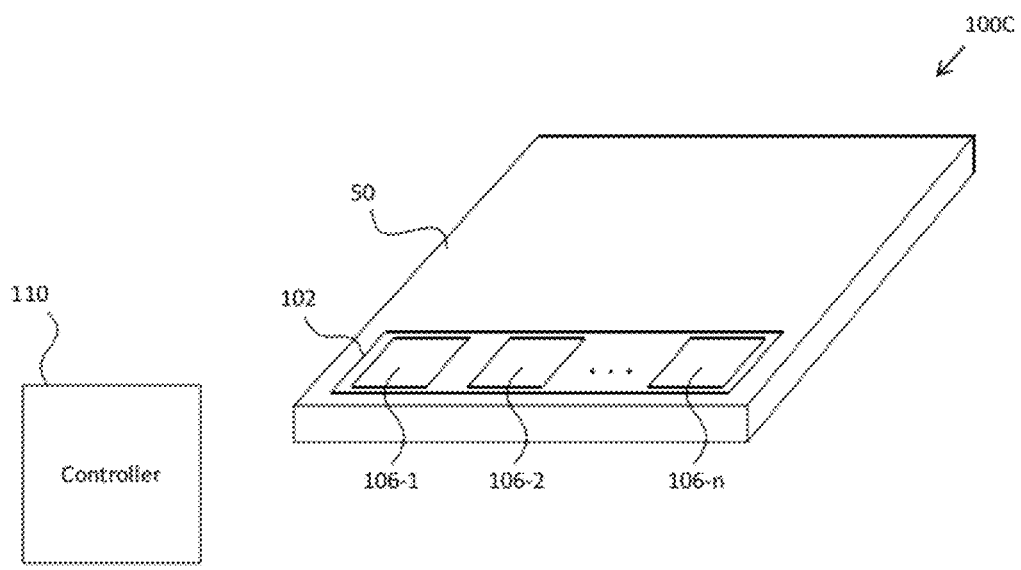
FIG. 1C illustrates another example of an improved magnetostriction inspection/testing system configured to inspect a plate.

FIG. 1A illustrates one example of an improved system 100A for non-destructive testing or inspection utilizing magnetostriction. As shown in FIG. 1, system 100A includes a magnetostrictive material 102 coupled to an object or structure 50 to be tested. Magnetostrictive/ferromagnetic material 102 may wrap or extend entirely around or across or at least partially around or across a common surface of object under test 50. In embodiments in which magnetostrictive material 102 does not wrap or extend entirely around or across object 50, a gap 101 may be defined by magnetostrictive material 102 as shown in FIGS. 1A and 1B. Examples of magnetostrictive/ferromagnetic materials include, but are not limited to, iron, nickel, cobalt, alloys of any one or more of such materials, and other materials that undergo magnetostriction, such as Terfenol-D and Galfenol. In some embodiments, test object 50 has a circular cross-sectional area having a perimeter length (e.g., a circumference) and a longitudinal length to define a cylinder.

An array 104 of two or more pulser/receiver coil circuits 106-1, 106-2, ..., 106-n ("pulser/receiver coil circuits 106") are placed on, or within close proximity to, a surface of magnetostrictive/ferromagnetic material 102. The magnetostrictive/ferromagnetic material 102 is temporarily or permanently coupled to a surface of the structure/object being tested 50. The array of pulser/receiver coil circuits 106 may completely encircle/extend across or partially encircle/extend across testing/inspection object 50. Each pulser/receiver coil circuit 106 is configured to receive and transmit voltage/current information from/to a controller 110.

In some embodiments, such as the embodiment illustrated in FIG. 1B, the magnetostrictive material 102 may be segmented such that there is no connectivity between the portions of magnetostrictive material 102 that reside below each individual pulser/receiver coil circuit 106. As shown in FIG. 1B, a plurality of gaps 101-1, 101-2, ..., 101-(n-1) are defined between adjacent magnetostrictive material segments 102-1, 102-2, ..., 100-n. Segmenting magnetostrictive material 102 reduces the generation of extraneous wave energy compared to embodiments in which magnetostrictive/ferromagnetic material 102 includes a single segment like in FIG. 1A.

A single magnet or a plurality of magnets 108-1, 108-2, ..., 108-n ("magnets 108"), which may be of a permanent magnet or generated by an electromagnetic nature (e.g. using an electromagnet, by a current-carrying wire wrapped around a ferromagnetic material, etc.), are placed within close proximity (e.g., less than or equal to one inch) to the magnetostrictive material and to each of the pulser/receiver coil circuits 106 such that the poles of each of the magnets 108 are directionally aligned. For example and as illustrated in FIG. 1A, for the generation and reception of torsional guided wave energy, each of the magnets 102 are arranged such that as one circles magnetostrictive material in a clockwise direction the north pole of a magnet 108 is encountered first and the south pole of the magnet is encountered second. One skilled the in the art will understand that the position of the magnets may be switched such that the south pole of a magnet 108 is encountered first and the north pole of the same magnet 108 is encountered second as one moves clockwise around magnetostrictive material 102. Furthermore, one skilled in the art will realize that the polarity of the magnets can be rotated so to generate and receive longitudinal guided wave energy. Magnet(s) 108 may be removed from system 100 once a bias magnetic field is induced in ferromagnetic material 102.

Figure 2:
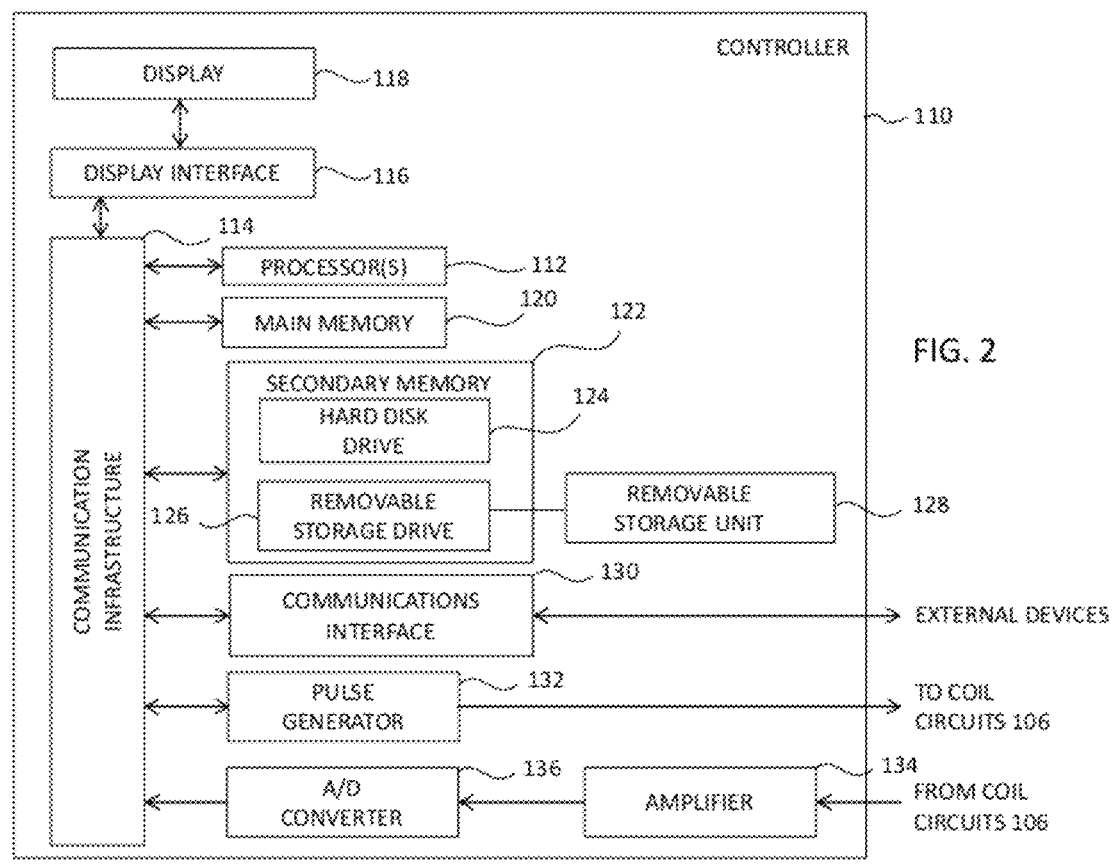
FIG. 2 illustrates one example of an architecture of a controller in accordance with the system illustrated in FIG. 1.

A controller 110 is in signal communication with each of the pulser/receiver coil circuits 106. FIG. 2 illustrates one example of an architecture of a controller 110. As shown in FIG. 2, controller 110 may include one or more processors, such as processor(s) 112. Processor(s) 112 may be any central processing unit ("CPU"), microprocessor, micro-controller, or computational device or circuit for executing instructions and be connected to a communication infrastructure 114 (e.g., a communications bus, cross-over bar, or network). Various software embodiments are described in terms of this exemplary controller 110. After reading this description, it will be apparent to one skilled in the art how to implement the method using other computer systems or architectures.

Controller 110 may include a display interface 116 that forwards graphics, text, and other data from the communication infrastructure 114 (or from a frame buffer not shown) for display on a monitor or display unit 118 that may be integrated with or separate from controller 110.

Controller 110 also includes a main memory 120, such as a random access memory ("RAM"), and may also include a secondary memory 122. Secondary memory 122 may include a more persistent memory such as, for example, a hard disk drive 124 and/or removable storage drive 126, representing an optical disk drive such as, for example, a DVD drive, a Blu-ray disc drive, or the like. In some embodiments, removable storage drive may be an interface for reading data from and writing data to a removable storage unit 128. Removable storage drive 126 reads from and/or writes to a removable storage unit 128 in a manner that is understood by one skilled in the art. Removable storage unit 128 represents an optical disc, a removable memory chip (such as an erasable programmable read only memory ("EPROM"), Flash memory, or the like), or a programmable read only memory ("PROM")) and associated socket, which may be read by and written to by removable storage drive 126. As will be understood by one skilled in the art, the removable storage unit 128 may include a computer usable storage medium having stored therein computer software and/or data.

Controller 110 may also include one or more communication interface(s) 130, which allows software and data to be transferred between controller 110 and external devices such as, for example, pulser/receiver circuit coils 106 and optionally to a mainframe, a server, or other device. Examples of the one or more communication interface(s) 134 may include, but are not limited to, a modem, a network interface (such as an Ethernet card or wireless card), a communications port, a Personal Computer Memory Card International Association ("PCMCIA") slot and card, one or more Personal Component Interconnect ("PCI") Express slot and cards, or any combination thereof. Software and data transferred via communications interface 130 are in the form of signals, which may be electronic, electromagnetic, optical, or other signals capable of being received by communications interface 130. These signals are provided to communications interface(s) 130 via a communications path or channel. The channel may be implemented using wire or cable, fiber optics, a telephone line, a cellular link, a radio frequency ("RF") link, or other communication channels.

In this document, the terms "computer program medium" and "computer readable medium" refer to media such as removable storage units 128, 130, or a hard disk installed in hard disk drive 124. These computer program products provide software to controller 110. Computer programs (also referred to as "computer control logic") may be stored in main memory 120 and/or secondary memory 122. Computer programs may also be received via communications interface(s) 130. Such computer programs, when executed by a processor(s) 112, enable the controller 110 to perform the features of the method discussed herein.

In an embodiment where the method is implemented using software, the software may be stored in a computer program product and loaded into controller 110 using removable storage drive 126, hard drive 124, or communications interface(s) 130. The software, when executed by a processor(s) 112, causes the processor(s) 112 to perform the functions of the method described herein. In another embodiment, the method is implemented primarily in hardware using, for example, hardware components such as application specific integrated circuits ("ASICs"). Implementation of the hardware state machine so as to perform the functions described herein will be understood by persons skilled in the art. In yet another embodiment, the method is implemented using a combination of both hardware and software.

Controller 110 also includes a pulse generator 132 configured to output a variety of pulses to pulser/receiver coil circuits 106. For example, pulse generator 132 may transmit time-delayed control signals to coil circuits 106, and/or pulse generator 132 may transmit control signals of varying amplitudes to coils 106. As will be understood by one skilled in the art, each separately controllable channel must have a corresponding pulse generator 132 that is coupled to one or more coils 142 (FIGS. 3B-3D) or to one or more pulser/receiver coil circuits 106 for active focusing.

An amplifier 134 is configured to amplify signals received from pulser/receiver coil circuits 106. Such signals received by coil circuits 106 include reflections of waves from structural features and other anomalies in test structure 50 in response to signals transmitted by pulse generator 132. An analog to digital ("A/D") converter 136 is coupled to an output of amplifier 134 and is configured to convert analog signals received from amplifier 134 to digital signals. The digital signals output from A/D converter 136 may be transmitted along communication infrastructure 114 where they may undergo further signal processing by processor(s) 112 as will be understood by one skilled in the art. For synthetic focusing, one skilled in the art will understand that a plurality of channels may be used in which each channel is coupled to a respective A/D converter 136, but each channel does not need to be connected to a respective pulse generator as in active focusing. One skilled in the art will understand that systems 100 may be configured to perform both active and synthetic focusing.

Figure 3A:
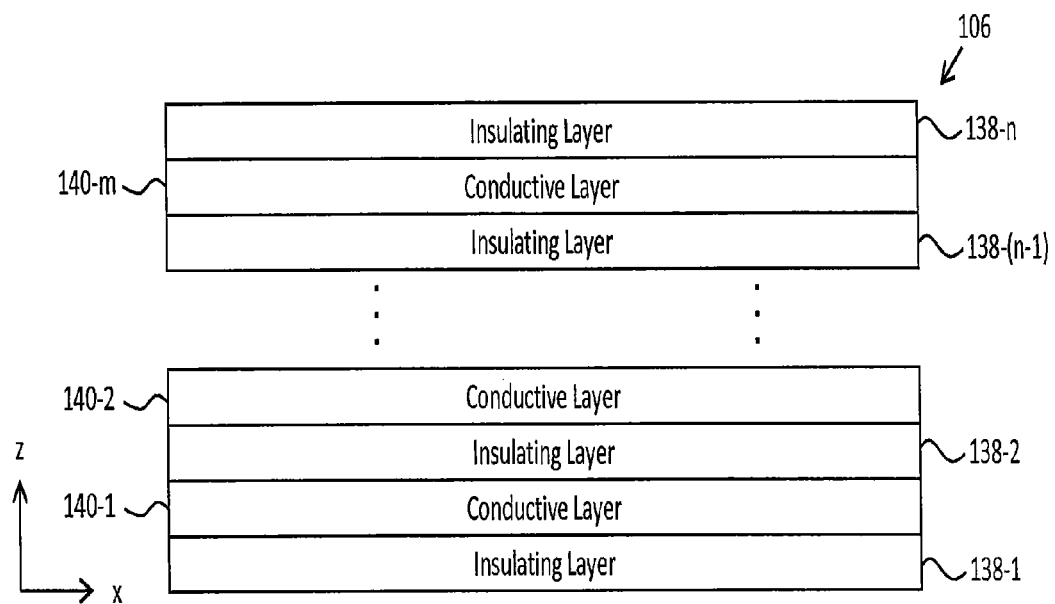
FIG. 3A is a cross-sectional side view of one example of a pulser/receiver coil circuit in accordance with the improved magnetostriction inspection/testing system illustrated in FIGS. 1A and 1B.

One example of a pulser/receiver coil circuit 106 is illustrated in FIGS. 3A-3D. FIG. 3A is a cross-sectional view a pulser/receiver coil 106 including a plurality of insulating layers 138-1, 138-2, . . . , 138-$n$ ("insulating layers 138") and a plurality of conductive layers 140-1, 140-2, . . . , 140-$m$ ("conductive layers 140") stacked in the z-direction in an alternating manner. Insulating layers 138 and conductive layers 140 form a printed circuit board ("PCB"). In some embodiments, the PCB is a flexible PCB and insulating layers 138 are formed from Mylar or other flexible insulating material, and conductive layers 140 are formed from copper or other conductive material.

Figure 3B:
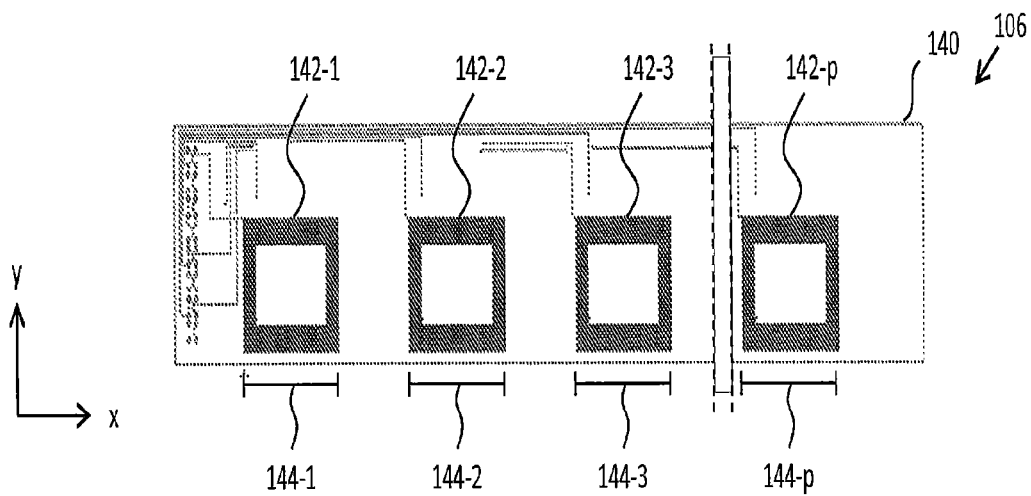
FIG. 3B is a plan view of the coils in a single conductive layer of a pulser/receiver coil circuit.

Each conductive layer 140 may include one or more coils 142 (comprising a loop of conductive material, such as copper) for producing a dynamic magnetic field in the magnetostrictive/ferromagnetic material in response to signals received from controller 110. FIG. 3B illustrates one example of a single conductive layer 140 including a number, p, of coils 142-1, 142-2, 142-3, . . . , 142-$p$ ("coils 142"). Coils 142 may be arranged in the conductive layer 140 such that coils 142 are aligned with one another in a first direction, e.g., a y-direction as illustrated in FIG. 3B, and spaced from one another in a second direction, e.g., in the x-direction.

Figure 3C:
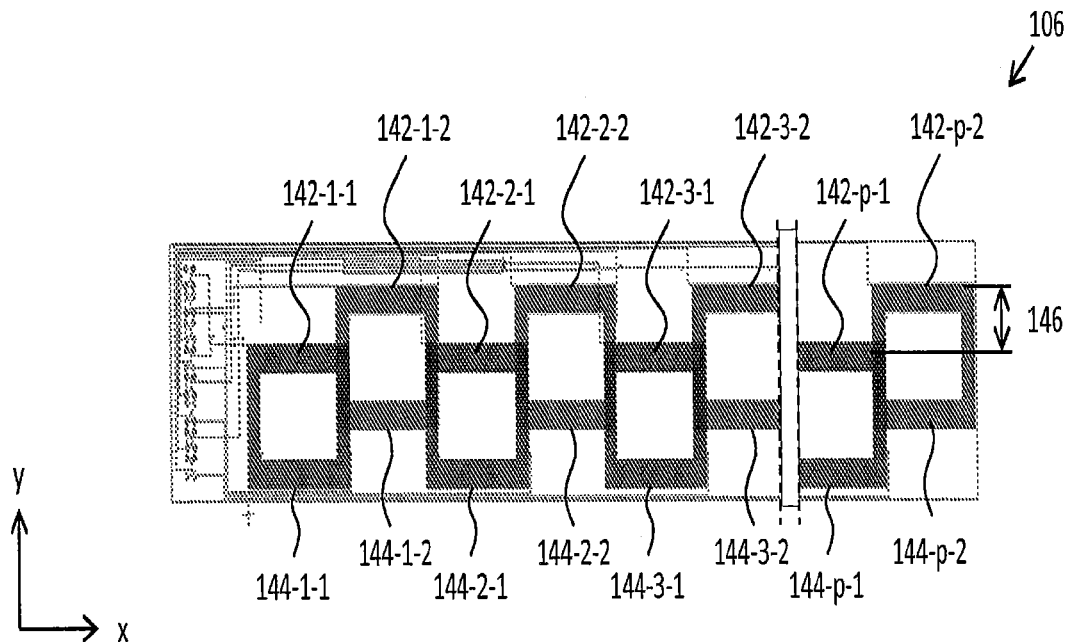
FIG. 3C is a plan view of the coils in two stacked conductive layers of a pulser/receiver coil circuit.

As arranged in FIG. 3B, coils 142 are configured to generate a wave that propagates in the y-direction as each coil 142 has a respective active area 144-1, 144-2, 144-3, . . . , 144-$p$ ("active areas 144") that extends perpendicular to a direction in which the generated wave propagates. The portions of coils 142 that extend parallel to the direction of propagation of the propagating waves, i.e., those portions of coils 142 that extend parallel to the y-direction, may be referred to as the ineffective areas of coils 142. FIG. 3C is a plan view of a pair of first and second conductive layers 140 each including a plurality of coils 142. In FIG. 3C, coils 142 in the first conductive layer 140-1 (those coils 142 ending with "-1" in FIG. 3C) are aligned with one another in the y-direction, and coils 142 in the second conductive layer 140-2 (those coils 142 ending with "-2" in FIG. 3C) are aligned with one another in the y-direction. The coils 142 in the different conductive layers 140-1, 140-2, which are conductively isolated from one another by an intervening insulating layer 138, e.g., insulating layer 138-2 in FIG. 3A, are arranged in the different conductive layers such that their ineffective areas overlap and so that their active areas 144 are not collinear, i.e., are offset as denoted by reference numeral 146. Offsetting the active areas 144 of coils 142 enables a wave to be generated in a single direction (e.g., towards the bottom of the page in FIG. 3C) as the wave propagating in the opposite direction (e.g., towards the top of the page in FIG. 3C) is canceled due to the offset and the manner in which the control signals received from controller 110 actuate coils 142.

Figure 3D:
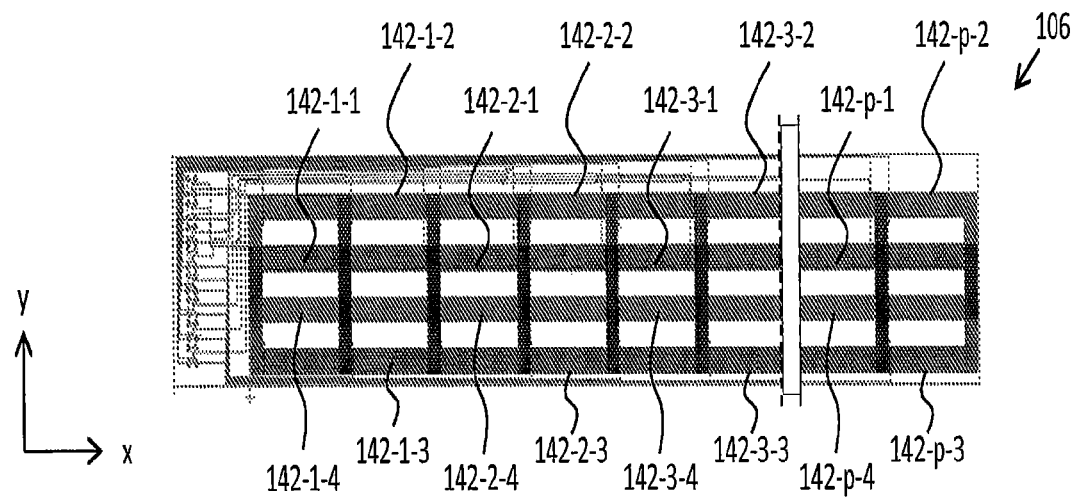
FIG. 3D is a plan view of the coils in a plurality of stacked conductive layers of a pulser/receiver coil circuit.

As described above, the number of conductive layers 140 that include coils 142 may be varied. For example, FIG. 3D illustrates an example of a pulser/receiver coil circuit 106 including four conductive layers 140 each including a plurality of coils 142. The coils in the first conductive layer 140-1 have reference numerals ending with '-1' and aligned in the x-direction with coils 142 disposed in the third conductive layer 140-3 (those coils with reference numerals ending with '-3') such that the active areas of the coils in the first and third conductive layers 140-1, 140-3 are collinear. The coils in the second conductive layer 140-2 are identified with reference numerals ending with '-2' and are aligned with the coils in the fourth conductive layer 140-4 (those coils with reference numerals ending with '-4') such that the active areas 144 of the coils are collinear. One skilled in the art will understand that the pulser/receiver coil circuits 106 may have its coils 142 disposed in a wide variety of manners and not merely the manner as described above with respect to FIGS. 3B-3D.

Stacking the ineffective areas of coils 142 as illustrated in FIGS. 3C and 3D such that the ineffective areas of coils 142 are minimized, which enables a greater area of ferromagnetic material to be utilized for generating wave energy for performing non-destructive testing. Additionally the stacking arrangement illustrated in FIGS. 3C and 3D reduces the amount of undesirable wave energy transferred into the object under test 50, such as that generated in the ineffective areas of the coils 142. Further reduction in the amount of undesirable wave energy transferred into the object under test 50 may be accomplished by removing the magnetostrictive/ferromagnetic material from under the ineffective areas of the coils 142 while aligning the active areas 144 of the coils 142 such that the active areas 144 are disposed over the magnetostrictive/ferromagnetic material 102.

In some embodiments, each pulser/receiver coil circuit 106, which may include coils 142 disposed in only a single layer, may correspond to a single channel such that all the coils 142 of a single pulser/receiver coil circuit 106 are coupled to a single pulse generator 132 and/or a single A/D converter 136. In some embodiments, a single pulser/receiver coil circuit 106, which have coils 142 disposed in a plurality of layers 140, may be controlled by a plurality of channels as some of the coils 142 may correspond to a first channel (e.g., driven by a respective pulse generator 132 and/or coupled to a respective A/D converter 136) and the other coils 142 of the same pulser/receiver coil circuit 106 may correspond to a second channel (e.g., driven by a respective pulse generator 132 and/or coupled to a respective A/D converter 136).

Figure 4:
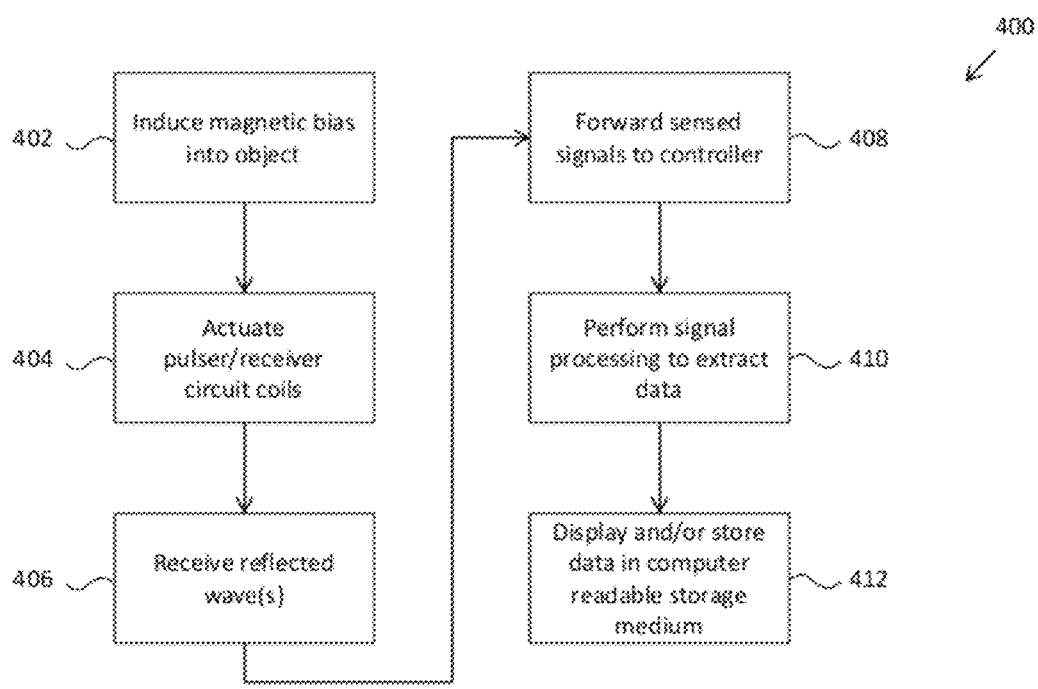
FIG. 4 is a flow diagram of one example of a method of performing non-destructive testing in accordance with the improved magnetostriction inspection/detection system illustrated in FIGS. 1A and 1B.

The operation of systems 100A, 100B, and 100C is described with reference to FIG. 4, which is a flow diagram of one example of a method 400 of magnetostrictive inspection/detection. As shown in FIG. 4, a magnetic bias is induced in magnetostrictive/ferromagnetic material 102 at block 402. The magnetic bias is induced by magnets 108 that are disposed on magnetostrictive material 102 such that their respective poles are directionally aligned such that a pole of a first type (e.g., a north pole) of a first magnet 108 is disposed adjacent to a pole of a second type that is opposite the first type (e.g., a south pole) of a second magnet that is disposed directly adjacent to the first magnet.

At block 404, one or more pulser/receiver coil circuits 106 are individually actuated by controller 110 to generate one or more guided waves in object 50. In some embodiments, controller 110 transmits time-delayed and/or amplitude controlled signals to each pulser/receiver circuit coil 106, which each alter the bias magnetic field in response thereby generating dimensional fluctuations in the magnetostrictive material 102 that is coupled to the object under test 50, resulting in the generation of guided waves in the object under test 50. The time-delayed and/or varying amplitude control signals may be transmitted to coils 106 from pulse generator 132 of controller 110.

By properly phasing the excitation of the pulser/receiver circuit coils 106, guided wave energy can be made to constructively interfere at a predetermined axial and circumferential location within object 50. The phasing can either be completed during excitation as described in the article "Angular-profile tuning of guided waves in hollow cylinders using a circumferential phased array" by Li et al. or via post-processing of the received data as described in the article "Defect imaging with guided waves in a pipe" by Hayashi et al. or as described in the article "Pipe inspection with guided wave synthetic focusing techniques" by Mu et al., the entireties of which are herein incorporated by reference. In embodiments in which object 50 has a non-cylindrical geometry such as, for example, a plate, an active or synthetic phased-array for plate and plate-like structures, such as illustrated in FIG. 3C, using Lamb or horizontal shear guided waves may be generated in object 50 as described in the article "Ultrasonic guided wave imaging techniques in structural health monitoring" by Yan et al., the entirety of which is herein incorporated by reference.

At block 406, pulser/receiver circuit coils 106 receive a reflected guided wave from structural features and/or other anomalies such as metal loss in object 50. As will be understood by one skilled in the art, guided wave energy may be sensed by pulser/receiver circuit coils 106.

The guided wave energy sensed by pulser/receiver circuit coils 106 are forwarded to controller 110 at block 408. The sensed guided wave energy may be received at amplifier 134 of controller 110 where amplifier 134 amplifies the received signals.

The amplified signals output of amplifier 134 are received at A/D converter 136. A/D converter digitizes the amplified signals it receives from amplifier 134 and outputs the digitized signals to communication infrastructure 114 where they are forwarded for further signal processing.

At block 410, the sensed signals undergo signal processing to extract relevant data. For example, the received signals may be processed to identify if the object 50 includes any defects or irregularities in the object 50. For example, the time-delays and/or amplitude controls are applied to the signals received by the pulser/receiver circuit coils 106 to artificially reconstruct the constructive interference of the excited guided waves at a specific location along the axis and circumference of the object 50.

At block 412, controller 110 may store the extracted data in a computer readable storage medium such as main memory 120 and/or secondary memory 122. Additionally or alternatively, the extracted data may be processed and displayed to a user on display 118 of controller 110.

Figure 5:
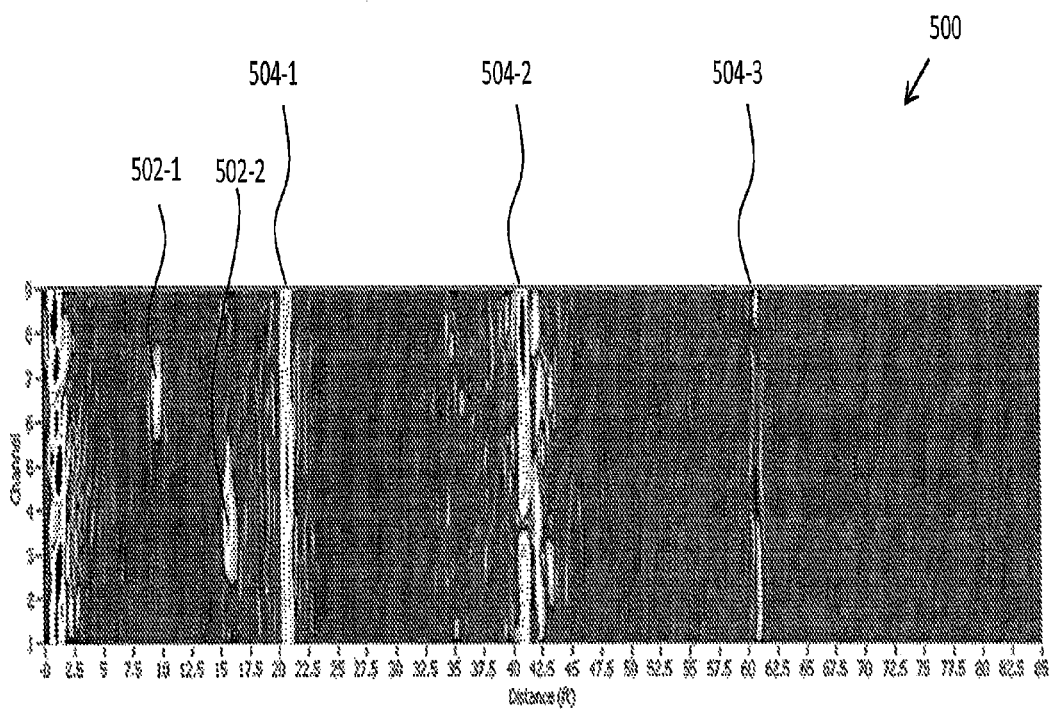
FIG. 5 is a sample unrolled pipe image/graphic using a synthetic focusing technique in accordance with the improved inspection system illustrated in FIGS. 1A and 1B.

FIG. 5 illustrates one example of a graphic 500 that may be displayed to a user of a system 100A, 100B based on data collected during a non-destructive inspection of a hollow cylindrical structure 50. Graphic 500 is an artificial reconstructed interference at multiple locations and has the appearance of a pipe split along the longitudinal axis and then unrolled to be displayed on a two-dimensional ("2D") plane. In particular, the vertical or y-axis of graphic 500 corresponds to a circumferential distance around object 50 which correspond to a location of a respective individually addressable channel implemented as a single pulser/receiver coil circuit 106 coupled to a surface of object 50. The horizontal or x-axis of graphic 500 corresponds to a distance along the longitudinal axis of object 50 from pulser/receiver coil circuits 106.

The synthetic focusing algorithms used in connection with system 100 advantageously enable graphic 500 to be displayed to a user, which enables the identification of defects and/or welds. For example and as illustrated in FIG. 5, two defect indications 502-1, 502-2 each having a different axial and circumferential location are visible as are circumferential welds 504-1, 504-2, 504-3. Each circumferential weld 504-1, 504-2, 504-3 wraps entirely around object 50 as shown by the defect extending from the top of graphic 500 to the bottom of graphic 500. Additionally, the relative amplitude of the reflections (e.g., the elevational differences in object 50) are indicated in the third dimension, such as with, but not limited to, an amplitude or color scale.

The improved non-destruction inspection systems and methods described above advantageously provide for the generation and reception of flexural guided wave modes using segmented magnetostrictive sensors for the inspection of hollow cylindrical structures. As a result of this capability, it is possible to distinguish reflections generated by structural features, such as welds, from reflections generated by material defects, such as metal loss. Furthermore, phased-array and synthetic guided wave focusing concepts can be employed using the segmented magnetostrictive sensor to determine the approximate circumferential location and extent of a reflection source thereby providing significantly improved sizing capabilities compared to conventional magnetostrictive sensors. By employing the focusing concepts with the segmented magnetostrictive sensor, improved SNR can be achieved through constructive interference of the wave energy generated and/or received by the individual segments of the sensor and can lead to improved sensitivity and penetration power.

The present invention can be embodied in the form of methods and apparatus for practicing those methods. The present invention can also be embodied in the form of program code embodied in tangible media, such as CD-ROMs, DVD-ROMs, Blu-ray disks, hard drives, or any other machine-readable storage medium, wherein, when the program code is loaded into and executed by a machine, such as a computer, the machine becomes an apparatus for practicing the invention. The present invention can also be embodied in the form of program code, for example, whether stored in a storage medium, loaded into and/or executed by a machine, or transmitted over some transmission medium, such as over electrical wiring or cabling, through fiber optics, or via electromagnetic radiation, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A system, comprising:
    at least one strip of ferromagnetic material induced with a bias magnetic field coupled to a surface of a structure under test; and
    a plurality of pulsing/receiving coil circuits aligned with a surface of the at least one strip of the ferromagnetic material,
    wherein the plurality of pulsing/receiving coil circuits are individually controllable by a number of channels to excite guided waves in the structure under test using at least one of active phased-array focusing or synthetic phased-array focusing of the guided waves.

2. The system of claim 1, further comprising a controller configured to receive reflected guided wave signals from the plurality of pulsing/receiving coil circuits and separate axisymmetric wave modes from flexural wave modes.

3. The system of claim 2, wherein the at least one magnet has its poles directionally arranged such that one or more of a family of torsional guided wave modes are generated by the at least two independent pulsing/receiving coil circuits.

4. The system of claim 2, wherein the at least one magnet has its poles directionally arranged such that one or more of a family of longitudinal guided wave modes are generated by the at least two independent pulsing/receiving coil circuits.

5. The system of claim 1, wherein the active phased-array focusing includes activating the plurality of pulsing/receiving coils circuits in one of a time-delayed or an amplitude-controlled manner to generate constructive interference of the guided waves at a predetermined location along a length of the structure under test.

6. The system of claim 1, wherein the synthetic phased array focusing includes applying at least one of time-delays or amplitude controls to reflected guided wave signals received by the plurality of pulsing/receiving coil circuits to artificially reconstruct a constructive interference of the excited guided waves at a specific location along a length of the structure under test.

7. The system of claim 1, further comprising a controller having a display configured to display a two dimensional representation of a three dimensional object such that surface variations of the structure under test are identifiable to a user.

8. The system of claim 1, wherein the at least one strip of ferromagnetic material includes a plurality of separate strips of ferromagnetic materials coupled to the surface of the structure under test.

9. The system of claim 8, wherein each of the independent pulsing/receiving coil circuits is aligned to a respective strip of ferromagnetic material.

10. A non-destructive inspection method, comprising:
    inducing a bias magnetic field in a ferromagnetic material coupled to a surface of a test structure;
    individually addressing a plurality of channels to actuate a plurality of pulser/receiver coils disposed on the ferromagnetic material to generate guided waves in the test structure using at least one of active phased-array focusing or synthetic phased-array focusing of the guided waves;
    receiving a reflected signal at one of the plurality of pulser/receiver coils; and
    processing the reflected signal to identify if the test structure includes an irregularity along its longitudinal length.

11. The non-destructive inspection method of claim 10, further comprising displaying a two dimensional representation of a three dimensional object such that the irregularity along the longitudinal length of the test structure is identifiable to a user.

12. The non-destructive inspection method of claim 10, wherein active phased-array focusing includes activating the plurality of pulsing/receiving coils circuits in one of a time-delayed or an amplitude-controlled manner to generate constructive interference of the guided waves at a predetermined location along a length of the structure under test, and wherein synthetic phased array focusing includes applying at least one of time-delays or amplitude controls to reflected guided wave signals received by the plurality of pulsing/receiving coil circuits to artificially reconstruct a constructive interference of the excited guided waves at a specific location along a length of the structure under test.

13. The non-destructive inspection method of claim 10, wherein the ferromagnetic material includes a plurality of separate strips of ferromagnetic material.

14. The non-destructive inspection method of claim 13, wherein each of the pulser/receiver coils is aligned to a respective strip of ferromagnetic material.

15. A system, comprising:
a ferromagnetic material coupled to a surface of a test piece, the ferromagnetic material having an induced bias magnetic field;
a plurality of pulsing/receiving coil circuits distributed on the surface of the test piece and aligned to a surface of the ferromagnetic material; and
a controller configured to individually control each of a plurality of channels each corresponding to at least one of the plurality of pulsing receiving coil circuits to excite guided waves in the test piece using at least one of active phased-array focusing or synthetic phased-array focusing of the guided waves.

16. The system of claim 15, further comprising a device for inducing the bias magnetic field in the ferromagnetic material.

17. The system of claim 15, wherein the controller is configured to output control signals to the plurality of pulsing/receiving coil circuits to generate at least one of a family of guided wave modes.

18. The system of claim 17, wherein the controller is configured to output control signals to the plurality of pulsing/receiving coil circuits in a time-delayed and/or an amplitude controlled manner to create constructive interference of waves at a predetermined location along a longitudinal length of the test piece.

19. The system of claim 18, wherein each of the plurality of coil circuits includes a plurality of coils.

20. The system of claim 19, wherein the plurality of coils in the plurality of coil circuits are disposed on at least two different layers of a multi-layer printed circuit board.

* * * * *